United States Patent [19]
Chen et al.

[11] Patent Number: 6,139,496
[45] Date of Patent: Oct. 31, 2000

[54] ULTRASONIC IMAGING SYSTEM HAVING ISONIFICATION AND DISPLAY FUNCTIONS INTEGRATED IN AN EASY-TO-MANIPULATE PROBE ASSEMBLY

[75] Inventors: James N C Chen, Chelmsford; Michael Atlas, Arlington, both of Mass.

[73] Assignee: Agilent Technologies, Inc., Palo Alto, Calif.

[21] Appl. No.: 09/302,776

[22] Filed: Apr. 30, 1999

[51] Int. Cl.[7] ...................................................... A61B 8/00
[52] U.S. Cl. ........................................... 600/437; 600/459
[58] Field of Search .................................. 600/437, 440, 600/441, 443, 447, 459; 73/626

[56] References Cited

U.S. PATENT DOCUMENTS

| | | | |
|---|---|---|---|
| 3,964,296 | 6/1976 | Matzuk | 73/626 |
| 4,246,792 | 1/1981 | Matzuk | 73/620 |
| 4,413,629 | 11/1983 | Durley, III et al. | 600/453 |
| 5,295,485 | 3/1994 | Shinomura et al. | 128/660 |
| 5,590,658 | 1/1997 | Chiang et al. | 128/661 |
| 5,617,864 | 4/1997 | Stouffer et al. | 128/662 |
| 5,722,412 | 3/1998 | Pflugrath et al. | 128/662 |
| 5,738,099 | 4/1998 | Chang | 128/662 |

*Primary Examiner*—Francis J. Jaworski

[57] ABSTRACT

An ultrasonic imaging system having an electronic control and signal processing circuit section interconnected with an improved probe assembly suitable for use in varied applications of ultrasonic imaging, especially in medicine, and in other fields of use. The probe assembly indudes an operator interface and a sensor head, both of which are structurally integrated within a compact housing according to a predetermined spatial relationship, such that an operator can position the probe assembly so as to locate the display adjacent the physical structure that is subject to isonification while simultaneously viewing, on the operator interface, an ultrasonic image of the physical structure. The ultrasonic image is thereby considered to be observable through an "acoustic window" that is implemented in the view provided in the operator interface.

26 Claims, 7 Drawing Sheets

ULTRASONIC IMAGING SYSTEM HAVING ISONIFICATION AND DISPLAY FUNCTIONS INTEGRATED IN AN EASY-TO-MANIPULATE PROBE ASSEMBLY

FIELD OF THE INVENTION

The invention generally relates to ultrasonic imaging systems and more particularly to an ultrasonic imaging system having a compact and easily manipulated probe assembly.

BACKGROUND OF THE INVENTION

Ultrasonic systems are known for detecting or imaging the internal structures of liquid, solid, and semi-solid materials. In operation, such apparatus typically include a handheld probe that generates a beam, of acoustic signals. The beam is transmitted into the material of interest and is reflected by various gradients or other physical features of the material. The beam may be focussed at various depths within the material and may also be scanned vertically and horizontally so that the reflected acoustic signals may be used to provide three-dimensional image data about various aspects of the material.

In a phased array ultrasound imaging system, the probe includes a transducer array of many transducer elements. Multiple-element transducer arrays consist of a plurality of individual piezoelectric elements, each of which typically features a separate electrical connection to each of paired electrodes. The system includes a multiple channel transmitter and a multiple channel receiver connected through a transmit/receive switch to the transducer. Each transmitter channel causes a selected transducer array element to transmit an ultrasound pulse into an object being imaged. The transmitted ultrasound energy is steered along a transmit scan line and is focused by applying appropriate delays to the pulses transmitted from each transducer array element, so that the transmitted energy adds constructively a desired focal point to form a transmit beam. A part of the transmitted ultrasound energy is reflected back to the transducer array by various structures that are in the path of the transmitted ultrasound energy.

The reflected ultrasound energy from an object or structure arrives at the array elements at different times. The received signals are amplified and are delayed in separate receiver channels and then are summed in a receive beam former to form a receive beam. The delay for each channel is selected such that the receive beam is steered at a desired angle and is focused at a desired depth. The delays may be varied so as to focus the beam at progressively increasing depths along a receive scan line as the ultrasound energy is received. Ultrasound energy may be transmitted along multiple transmit scan lines in a desired scan pattern, such as a sector scan, and the received signals are processed to produce an image of the region of interest. In a particular application of ultrasonic systems in the field of medicine, ultrasonic probes are manipulated for examination of the anatomical parts of a patient. For example, the reflected signals may be received, analyzed, and processed to produce an image display that is representative of the structure of an internal organ, such as the heart.

Modern ultrasonic diagnostic systems have been developed to provide advanced features, such as electronic beam steering and electronic focussing, by using complex electronics for effecting beam forming channels to control the amplitude and phasing of, for example, a one-dimensional (linear array) or two-dimensional (matrixed array) arrangement of transducer elements. The emission of an individual acoustic signal channel in a typical array will require that a transducer element be coupled with a signal provided on a respective beam forming channel. Therefore, in most applications, a large number acoustic signal channels is desirable to provide high resolution acoustic imaging.

Accordingly, a modern diagnostic ultrasound system includes a rather bulky probe having at least one transducer array that features a large number of separate transducer elements, a cable for handling a large number of signals, an electronics unit for supporting the large number of beam forming channels necessary to provide high resolution acoustic imaging. A remotely-located display unit is used for generating the high resolution acoustic image.

Accordingly, one conventional approach to improving the modern diagnostic imaging system is to connect a large number of signal cables to a transducer element array fixed in a compact housing. The probe typically includes a sensor head containing one or more ultrasonic transducer element arrays whereby the transducer elements are electrically connected to an intermediate circuit housed in the sensor head by a short flexible circuit or a connector. The signal cables are provided in a multiconductor cable that is electrically connected to the intermediate circuit, which transmits electrical signals between the transducer array and a signal processing and display apparatus that is connected to the distal end of the cable.

Another approach attempts to miniaturize and integrate some or all of the components of a diagnostic imaging system so as to integrate those components in a portable, handheld unit. That is, such an approach intends to integrate the transducer, cabling, beam former, image processing electronics, display, power source, etc. in a single package. See, for example: U.S. Pat. No. 3,964,296, entitled "Integrated Ultrasonic Scanning Apparatus", and issued to Matzuk; U.S. Pat. No. 4,246,792, entitled "Self-contained Ultrasonic Scanner", and issued to Matzuk; U.S. Pat. No. 5,295,485, entitled "Ultrasonic Diagnostic System", and issued to Shinomura et al.; U.S. Pat. No. 5,617,864, entitled "Method and Apparatus for Positioning an Ultrasonic Transducer and a Display Screen", and issued to Stouffer et al.; U.S. Pat. No. 5,722,412, entitled "Handheld Ultrasonic Diagnostic Instrument", and issued to Pflugrath et al., and U.S. Pat. No. 5,738,099, entitled "Portable Ultrasonic Diagnostic Apparatus", and issued to Chang. This approach adds that is said to result in is a portable unit that is described as "hand-held". However, an examination of the literature shows that such "hand-held" units would appear to be, in practice, difficult to manipulate by less than two hands without assistance. For example, U.S. Pat. No. 3,964,296 describe the use of a support arm mechanism; U.S. Pat. Nos. 5,617,864 and 5,738,099 include a pistol grip or a counter balance device to alleviate the user fatigue associated with manipulation of the apparatus.

Furthermore, some of the foregoing approaches, in an attempt to integrate all of the functions of the diagnostic imaging system into a single portable unit, result in a unit that is likely to be more complex and expensive than is necessary or desirable for some applications. See, for example, U.S. Pat. Nos. 4,246,792 and 5,722,412.

Robustness and reliability are also a concern. A handheld unit can be subject to impact shock, temperature extremes, and other undesirable physical and environmental conditions that ordinarily would not be experienced by those components if they were located in a rack-mounted unit. Accordingly, an attempt to integrate all of the functions of a diagnostic imaging system into a single handheld unit forces the designer to resort to difficult and costly techniques to assure that all of the integrated components meet a diversity of opposing constraints, such as of low weight and mass, high reliability, low-cost, and ease of manipulation.

Hence, there remains a need for an ultrasonic diagnostic imaging system having a probe assembly that incorporates a display and transducer within a single unit, so that the operator can easily view a displayed image while positioning the transducer, wherein the probe assembly is reliable in operation and is small, durable, simple, and inexpensive to construct. There is a further need for such a probe assembly that is integrated in a lightweight package that is susceptible of being manipulated by the fingers of one hand, preferably by grasping the unit between the thumb and forefinger, in order to be easily manipulated by one hand without fatigue. Such a probe assembly would allow the operator to devote one hand to the task of effectively positioning the probe assembly for diagnostic utility, thus freeing the other hand for, e.g., palpitation of the tissue that is being examined, or for operating the controls of the imaging system, or for other tasks. Additionally, such a probe assembly would be especially useful if configured for operation in a confined space, such as in a small body cavity.

SUMMARY OF THE INVENTION

The present invention provides an ultrasonic imaging system having an electronic control and signal processing circuit section interconnected with an improved probe assembly suitable for use in varied applications of ultrasonic imaging, especially in medicine, and in other fields of use.

A probe assembly constructed according to the present invention includes an operator interface and a sensor head both of which are structurally integrated within a compact housing according to a predetermined spatial relationship. The probe assembly includes an operator interface and a sensor head, both of which are structurally integrated within a compact housing according to a predetermined spatial relationship, such that an operator can position the probe assembly to locate the display adjacent a physical structure (s) that is subject toisonification while simultaneously viewing, on the operator interface, an ultrasonic image of the physical structure. The ultrasonic image is thereby considered to be observed through an "acoustic window" that is implemented in the view provided in the operator interface. Accordingly, the operator may carry out the tasks of viewing the image and positioning the transducer simultaneously, in a fashion that is intuitive and free of the distraction or interruption of having to shift his or her attention between the probe and a separate, remotely-located operator interface.

The preferred embodiment of the probe assembly: a) integrates the respective functions of the transducer array and the operator interface into a single assembly that can be easily manipulated by one hand; b) structurally fixes the operator interface in a spatial relationship with the transducer array so as to afford a novel "acoustic window" of the physical structure(s) that are subject to ultrasonic energy emitted by the transducer array; and c) is designed to be easier, more robust, more reliable, and less expensive to construct than the "hand-held" imaging systems found in the prior art.

A preferred embodiment of the contemplated probe assembly includes a housing, a signal interconnection means, a sensor head having at least one transducer element array, an operator interface having a display, and an intermediate circuit for effecting electrical connection between the signal interconnection means, the sensor head, and the operator interface.

In a first preferred embodiment of the invention, the operator interface, sensor head, and intermediate circuit are integrated in a single oblate housing located at the distal end of a flexible cable portion. A sheath on the cable portion is joined to a radial extension of the housing; the sheath and the extension of the housing are preferably formed of a shaped polymer extrusion to provide a lightweight, watertight joint. The extension preferably includes opposing concave depressions that accommodate the fingers of the operator when the housing is grasped in one hand. The housing may also include additional features for encouraging a secure, one-handed grip on the housing, such as several circumferentially raised ribs of resilient material.

The compact size of the housing and the simplified fashion in which the flexible cable is joined with the extension of the housing allows the probe assembly to be manufactured as a compact, lightweight, inexpensive, and easily manipulated unit. Furthermore, preferred embodiments of the probe assembly may be constructed to withstand sterilization by chemical treatments or immersion in cleanser, disinfectant, or other solutions.

A particular feature of a probe assembly constructed according to the present invention is that the operator interface and the sensor head are structurally integrated within a compact, lightweight, and ergonomic housing such that the probe assembly is considered to be "hand-held", wherein that term is intended herein to describe a probe assembly that is susceptible to successful positioning, with respect to a region of interest, by the use of only one hand.

In another feature of the present invention, the operator may observe the physical structure(s) that are subject to isonification through the "acoustic window" in a fashion whereby the operator's hand-to-eye coordination is greatly enhanced.

In another feature of the present invention, preferred embodiments of the transducer probe assembly combine many of the benefits expected from the prior art "handheld" ultrasonic imaging system described hereinabove, such as the integration of a display and transducer in a single unit, with many of the attributes expected from a conventional rack-mount (or similar) ultrasonic imaging system, such as suitable electronics for effecting high resolution display, electronic beam steering, electronic focusing, and the like. For example, the electronic circuits necessary for operation of the contemplated ultrasonic imaging system need not be integrated in the probe assembly and in fact are preferably connected to the probe assembly by way of the signal interconnection means. Hence, an operator can operate the contemplated transducer probe assembly with one hand more easily than can be accomplished with either the conventional handheld ultrasonic imaging system, or the ultrasonic probe typically associated with a conventional rack mount (or similar) imaging system.

In another feature of the present invention, the probe assembly includes an intermediate circuit assembly that connects the flexible cable and the operator interface and the transducer element array by way of respective first and second flexible circuits, thereby eliminating the need for any additional means of connection. This reduces the size and weight of the probe assembly to a size suitable for applications such as those involving insertion into confined spaces, such as small body cavities.

In another feature of the present invention, the probe assembly may optionally include a second operator interface having a second display so as to afford a second respective acoustic window.

In another feature of the present invention, the probe assembly may be constructed to position the display and the sensor head in a predetermined spatial relationship wherein the display and the sensor head are spaced apart and coaxially aligned.

In another feature of the present invention, the probe assembly may be constructed to position the display and the sensor head in a predetermined spatial relationship wherein the display and the sensor head are spaced apart and are laterally offset.

In another feature of the present invention, the probe assembly is adapted for construction using automated techniques, e.g., the intermediate circuit assembly may be connected directly to the operator interface and/or transducer element by advanced manufacturing techniques such as thermosonic welding, thereby facilitating automated manufacture of the probe assembly. As a result, preferred embodiments of the contemplated probe assembly are simple and inexpensive to produce.

BRIEF DESCRIPTION OF THE DRAWINGS

The foregoing and other features and advantages of the invention will be apparent from the following more particular description of preferred embodiments of the drawings in which like reference characters referred to the same parts throughout the different views. The drawings are not necessarily to scale, emphasis instead being placed upon illustrating the principles of the invention.

DETAILED DESCRIPTION OF THE PREFERRED EMBODIMENT

Figure 1:
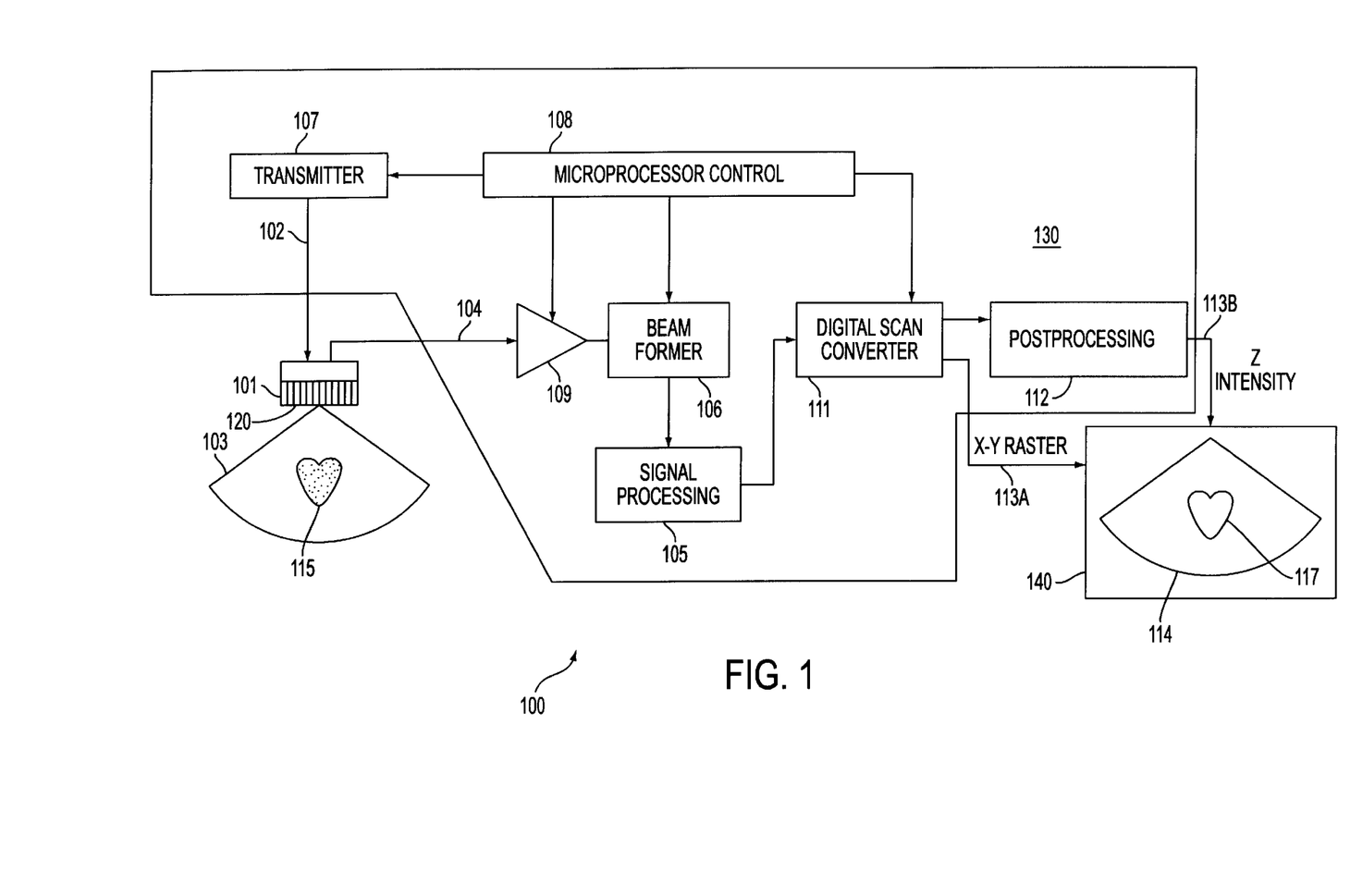
FIG. 1 is a simplified schematic representation of a preferred embodiment of a ultrasonic imaging system constructed according to the present invention.

FIG. 1 shows an ultrasound imaging system 100 constructed according to the present invention and having a sensor head 120, an interconnected control and signal processing circuit section 130, and an operator interface 140. An electrical stimulus 102, such as a pulse, is provided on a signal line 118 to an array 101 of transducer elements, causing the array 101 to transmit an ultrasonic acoustical wave 103. Isonification ensues as the ultrasonic wave is transmitted into a region of interest and eventually, at least partially, is reflected by a physical structure in the region of interest. In the illustrated embodiment, the region of interest lies within a human body and the physical structure is a heart 115. The reflected wave ("echo") is received by the transducer array 101 which produces an echo signal on signal line 104. The echo signal is representative of one or more characteristics of the physical structure. Various properties of this echo signal, such as its amplitude and phase, are then analyzed by a signal processing section to determine information about the object, such as its size, location, and velocity. See for example U.S. Pat. No. 5,060,651, U.S. Pat. No. 5,301,168, and U.S. Pat. No. 5,462,057, the contents of which are incorporated herein by reference.

FIG. 1 shows a control section 108 for controlling each of a transmitter 107, receiver 109, multichannel beam former 106, and digital scan converter 111. The echo signal 104 from transducer array 101 is sent to the preamplifier 109 and then in series to beam former 106, signal processor 105, and digital scan converter 111. The z-component of a display signal is sent on a z-intensity line 113B to post processor 112, and the resulting z-intensity is displayed on a suitable display in the operator interface 140. The x-y component of a display signal is sent via x-y raster line 113A and displayed on a suitable display in the operator interface 140. Lines 113A, 113B, 118 are collectively provided in a signal interconnection means according to methods and apparatus known in the art, such as by use of a flexible cable, or by wireless means such as a suitable combination of optical or radio frequency transceivers and related circuits.

It will be recognized that other embodiments of the control and data-processing circuit 130 may be constructed as known to those skilled in the art. In particular, the control and data-processing of the first and second signals described herein may be carried out by other transmitting and imaging processing techniques without departing from the teachings of the present invention.

According to a principal feature of the present invention, and in a significant departure from the prior art, the ultrasound imaging system 100 integrates the operator interface 140 and the sensor head 120 into a single, compact, and lightweight unit so as to provide a transducer probe assembly that provides both isonification and image display in a single housing. According to a second principal feature of the present invention, the contemplated probe assembly is easily manipulated by use of one hand. Because the contemplated transducer probe assembly is connected to the control and signal processing circuit section 130 by way of the aforementioned signal interconnection means, the operator can orient the probe assembly with respect to a physical structure 115 to be isonified and simultaneously observe the resulting ultrasonic image 117 provided in a view 114 on the operator interface 140. The operator may thereby position the probe assembly without the distraction or interruption of having to shift his or her attention between the transducer probe assembly and a separate, remotely-located display unit.

Furthermore, and according to still another principal feature of the present invention, the contemplated probe assembly integrates the sensor head 120 and the operator interface 140 within a single housing according to a predetermined spatial relationship such that the image 117 appears within the view 114 in real-time (or near real-time) when the probe assembly is suitably positioned for isonification of the physical structure 115. The image 117 thus appears within an "acoustic window" implemented on the operator interface 140; this image 117 will change in accordance with changes in the location and orientation of the probe assembly with respect to the physical structure during such isonification. Hence, for the purposes of the description herein, the term "acoustic window" is defined as the realization of an view (such as a view of 114) derived from the operation of a sensor head (such as sensor head 120) and an operator interface (such as operator interface 140), wherein the operator interface and the sensor head are structurally integrated in a probe assembly, and wherein the operator interface and the sensor head are aligned in a predetermined spatial relationship for the purpose of spatially associating the view displayed on the operator interface with the actual location of the physical structure that is subject toisonification. In other words, the acoustic window implemented by the novel probe assembly simulates a view of the physical structure as if the operator could look "through" the acoustic window, into the region of interest, to see the physical structure. For example, slow changes in the position and orientation of the probe assembly with respect to a region of interest (e.g., the neck, torso, etc. of a patient) thus allows the operator to thereby to scan, discover, locate, and (with continued isonification, if desired) monitor one or more aspects of the physical structure 115 according to its appearance as an image 117 in the view 114. As a result, the probe assembly functions as a visualization tool for discovering and monitoring the actual location of the physical structure 115 (and for observing in real-time, or in near real-time, other aspects of the physical structure).

Without the predetermined, spatial association between the position and orientation of the probe assembly and the physical structure to be isonified, the actual location and dimensions of the physical structure would otherwise be difficult to discern by the operator. One of the several benefits of this spatial association feature is that the operator may, after discovering the actual location of the physical structure, then rely on this information and accordingly proceed with one or more useful medical or diagnostic techniques, such as: palpitation of the tissue at the location of the physical structure; application or injection of medication destined for the physical structure; perform massage, thermal, radiation, or other therapeutic treatments on the physical structure; perform surgical (including pre-operative and post-operative) or radiological procedures that may be necessary at the location of the physical structure; and the like. Furthermore, because the probe assembly is contemplated as being easily manipulated by one hand, the operator has a free hand so as to assist in, or perform, such medical and diagnostic techniques without interruption of the isonification and viewing of the physical structure.

Figure 2:
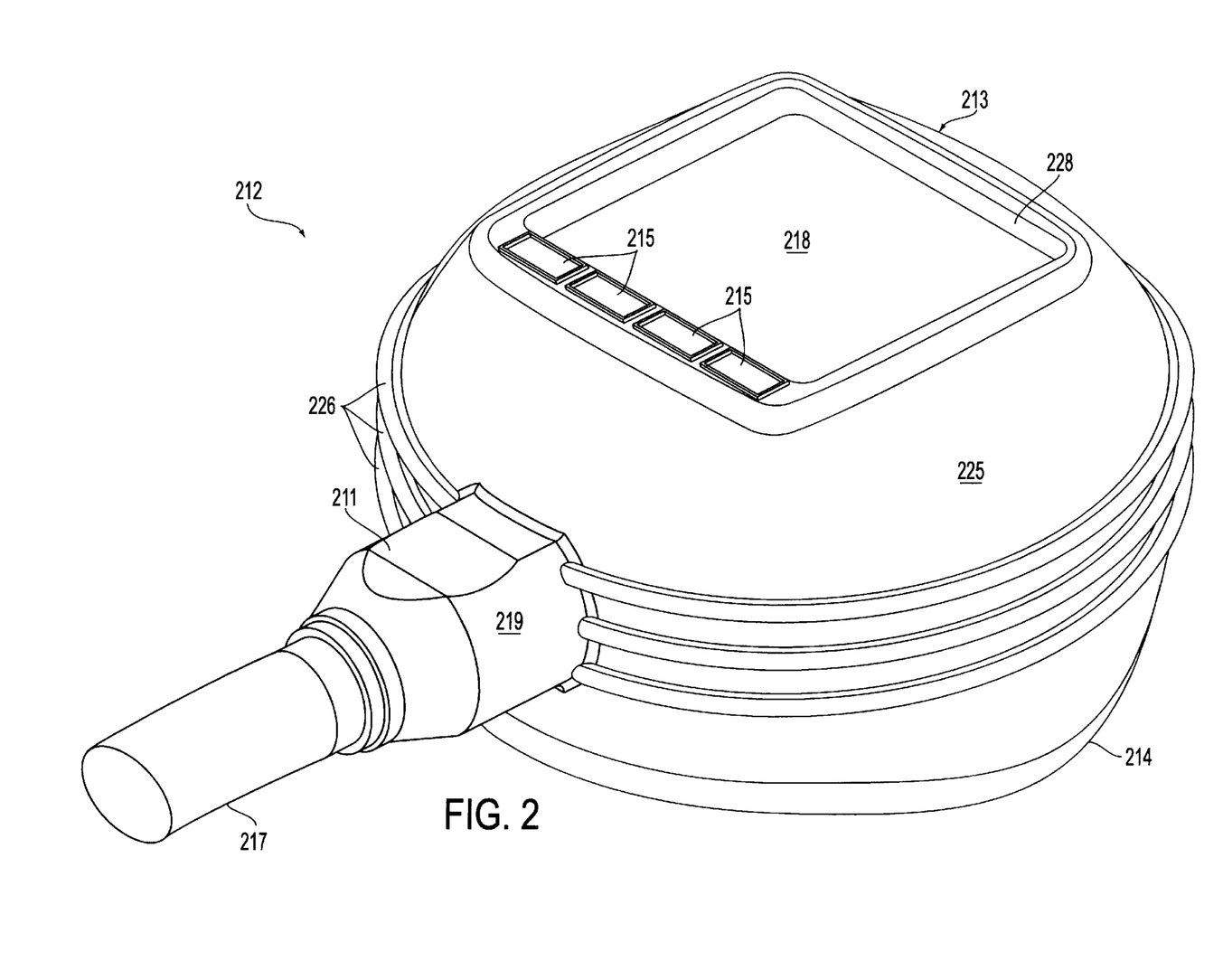
FIG. 2 is a simplified side perspective view of a first preferred embodiment of a novel ultrasonic probe assembly constructed according to the present invention for use in the system of FIG. 1.
Figure 3:
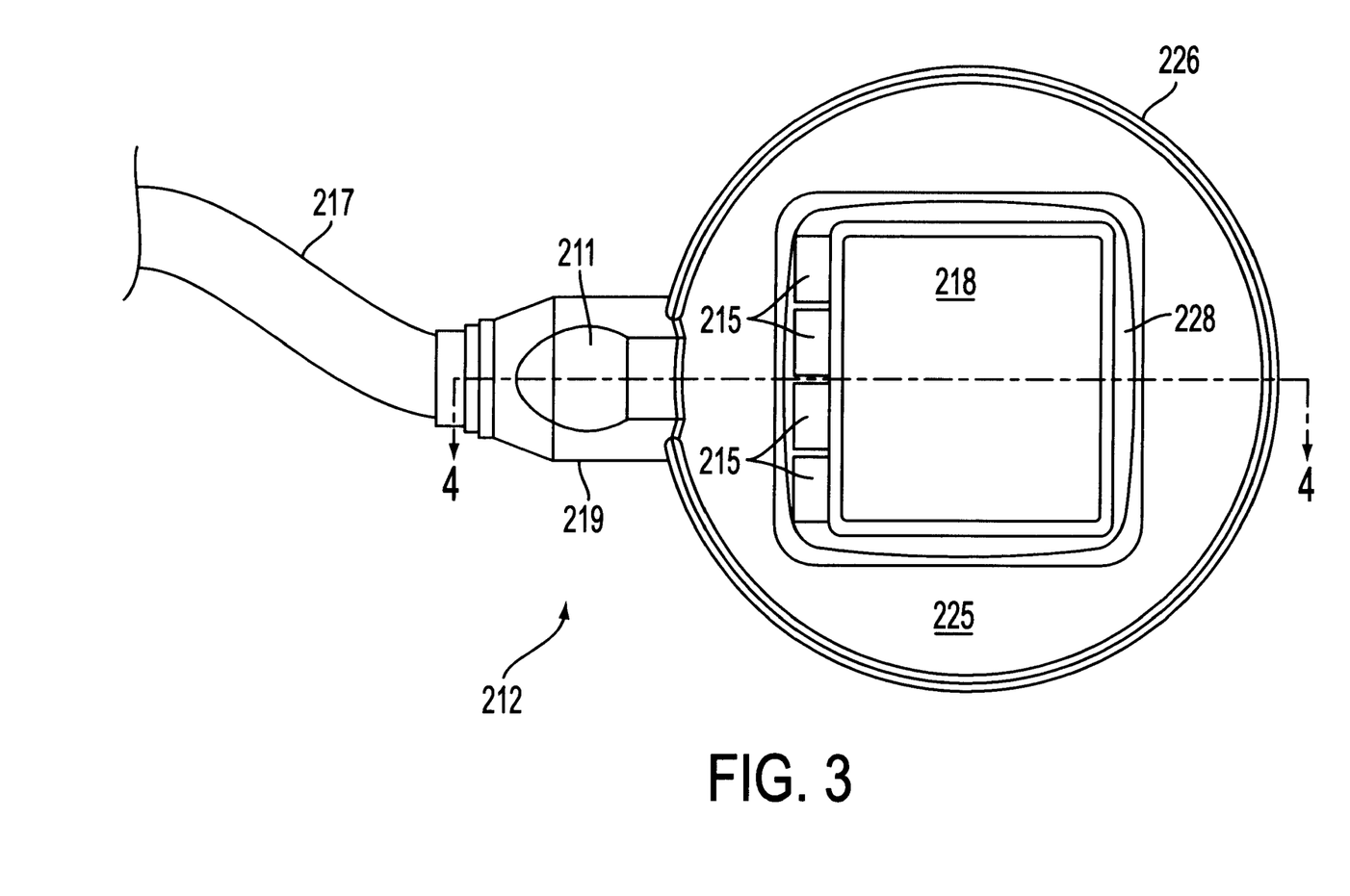
FIG. 3 is a plan view of the ultrasonic probe assembly of FIG. 2.
Figure 4:
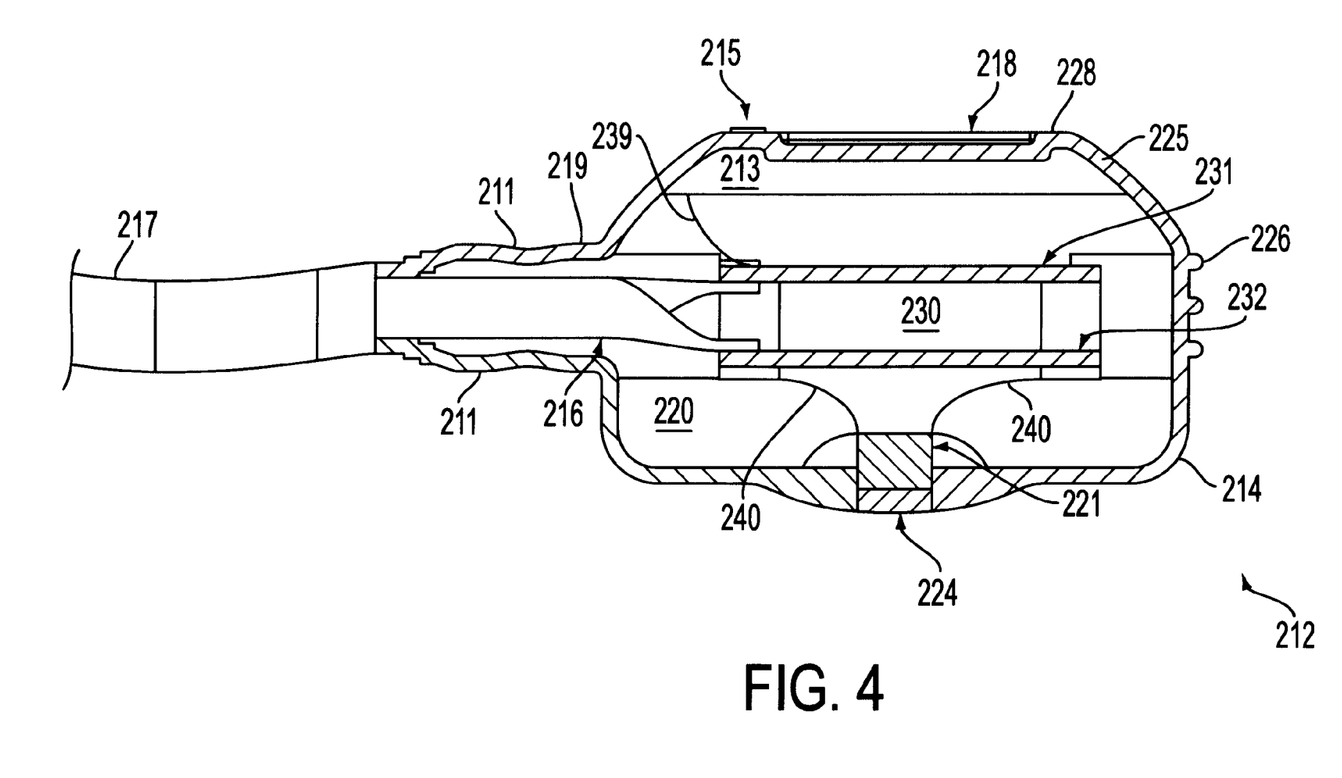
FIG. 4 is a side sectional view of the ultrasonic probe assembly of FIG. 3.

As shown in FIGS. 2–4, a first preferred embodiment of an ultrasonic probe assembly 212 is constructed to incorporate certain active components of the probe assembly 212 within a housing 225. These components are connected to the remainder of the system 100 by way of a flexible cable 216. The active components of the probe assembly 212 include: an operator interface 213 having a display 218 and data input means such as keys 215; an intermediate circuit 230 having first and second circuit boards 231, 232; and a sensor head 214 having a transducer array section 220 that includes a transducer array 221, flexible circuits 240, and an acoustic lens 224. The operator interface section 213 allows the operator to view a diagnostic image on the display 218 and, when necessary, to input data, command, and control signals as may be desired for effecting zoom, contrast, and similar adjustments by use of one or more of the keys 215. Preferably, the keys 215 are located adjacent the display 218, both of which are connected to the first circuit board 231 by a flexible circuit 239. The keys 215 are preferably provided in the form of touch-sensitive or membrane keys that are sealed against the potential intrusion of fluids or other matter. The display 218 is preferably provided in the form of a miniature liquid crystal display having a bezel 228 that allows adjustment (e.g., rotation) of the orientation of the display 218. It is contemplated that the display 218 is operable to render not only a diagnostic image, but in certain modes to display one or more symbolic or alphanumeric characters which relate to the operation of the diagnostic imaging system 100 and which inform the operator of information relevant to the operation of the keys 215 (such as "zoom", "contrast", "rotate", etc.), or of information relevant to the operation of the display 218, or of another system component. For example, successive actuation of one of the keys may be used to rotate the image shown on the display in 90 degree increments to allow an operator to view the image from an off-angle position.

The preferred embodiment of the illustrated probe assembly 212 allows the flexible cable 216 to be joined at a radial tubular extension 219 of the housing 225. This joint may be permanent or reversible, according to the application, by use of appropriate connectors (not shown) located within the extension 219 for effecting a suitable mechanical and electrical connection as known in the art. The extension 219 includes finger grips 211 preferably provided in the form of a pair of opposing depressions each of which are configured to receive finger pressure such that the extension 219 may be easily grasped between a thumb and a forefinger. The flexible cable 216 includes a protective sheath 217 which preferably is sealed to the extension 219 in a fluid tight connection so as to protect the conductors within the cable 217 and the various components located within the housing 225 from the environment. The flexible cable 216 and the extended portion 219 of the housing 225 are thereby mechanically secured within the sheath 217. The sheath 217 may optionally extend onto certain portions of the housing 225 so as to provide not only a secure connection of the cable 216 to the housing 225 but also to provide a resilient, friction-enhanced surface adapted for improving one's grasp on the housing 225. Sheath 217 can be made of biocompatible polymers such as polyethylene. In the illustrated embodiment, the housing 225 is provided in the form of a lightweight, oblate shell so as to be easily cupped or grasped between the thumb, index finger, and forefinger of a single hand. Of course, the housing 225 may be provided in other shapes or configurations suitable for this task. Preferably, certain versions of the probe assembly 212 would be manufactured so as to withstand immersion in a sterilization chamber, and to withstand the coupling fluids or gels used in some ultrasonic diagnostic imaging techniques. Certain other versions of the probe assembly 212 may be manufactured so as to withstand the presence of fluids, dust, debris, and the like that may be expected in an adverse environment, e.g., when the probe assembly 212 is deployed in an industrial setting, outdoors, etc.

The transducer array 221 is connected to the second circuit board 232 by way of first and second flexible circuits 240. The transducer array 221 may be driven by a drive signal supplied by the transmitter 107 and carried by the conductors in the cable 216 to switching circuits (suitable multiplexing and demultiplexing circuitry) located on the second circuit board 232 such that an acoustic signal is emitted from the sensor head 214.

The emitted acoustic signal is preferably coupled by use of appropriate transducer gel material to the region of interest upon which the sensor head 214 may be impressed. The emitted acoustic signal is subject to a combination of reflection, scattering, and absorption by the physical structures that are present in the region of interest. The transducer array 221 is operated to transduce a returning acoustic signal that is indicative of the structural aspects of one or more physical structures in the region of interest. The returning acoustic signal is transduced to an electronic signal, which is then passed through switching circuitry on the second circuit board 232 and sent to the receiver 109.

Data representative of the physical structure may be converted to information provided in a signal that is then returned to the probe assembly 212 by way of the cable 216 so as to be connected as appropriate display driver signals to the display 218 by display driver circuits on the first circuit board 231. The drive signals are provided to the display 218 for effecting graphical representation of the information on the display 218 for viewing by the operator according to ultrasonic image signal processing and display techniques known in the art. Also, as previously described, additional data representative of symbolic or alphanumeric characters relevant to system operation may be generated by the microprocessor 108 in a similar fashion and provided to the first circuit board 231 and to the display 218 for viewing by the operator. A liquid crystal display (LCD) C, Sixpanel suitable for the display 218 is commercially available from Kopin Corp, of Taunton, Massachusetts in the form of a standard resolution 320x240 pixel display or a VGA (640× 480 pixel display) version.

Flexible circuits 239 are preferably utilized respectively for connections between the first and second circuit boards 231 and the operator interface 213; flexible circuits 240 are utilized respectively for connections between the second circuit boards 232 and the transducer array 221. The flexible circuits 239, 240 may be constructed to include a flexible substrate composed of an electrically insulating polymer such as polyimide and plural conductor traces having exposed leads. The flexible circuit 240 is configured for obtaining an electrical connection at the appropriate metalization layers within the transducer array 221.

The transducer array 221 preferably includes a plurality of activatable elements that are operable for transmission and reception of acoustic beams formed by, e.g., the switching of each element in a phased array format. The transducer array 221 is generally made of piezoelectric materials, such as lead zirconate titanate (PZT) ceramic. It may also be formed of "composites", in which a piezoelectric ceramic and a polymer are combined for an improved range of properties. Suitable imaging transducer arrays have also been made of electrostrictive materials, which are highly polarizable by the application of a DC bias voltage. Lead magnesium niobate-lead titanate (PMN-PT) is one example of an electrostrictive ceramic. Electrode layers that overlying and underlying each active element enables each element to be individually and electrically addressed by use of the flex circuits 240.

An acoustic matching layer (not shown) may be included to provide an acoustic impedance transition between the transducer array 221 and an optional acoustic lens 224. The desired emission of the transducer array 221 from the lens 224 is considered as emanating from the "forward" or underside of the probe assembly 212; the operator interface 213 is generally considered as located at the "rear" or upper side of the transducer 200. The transducer array 221 is typically subject to unwanted, rear-transmitted acoustical emissions that emanate from the backside of the transducer array 221 and into the housing 225. The rear portion of the transducer array 221 therefore preferably includes an integral acoustic absorber formed of an appropriate transducer backing material selected from those known in the art.

The probe assembly 212 may also include other items known in the art, which are omitted from the Figures for clarity, such as a transducer support structure, heat sink, or a combination thereof.

While the transducer array 221 is illustrated herein as being substantially planar, it should be understood that it need not be strictly flat. In alternative embodiments of the invention, the transducer elements may comprise major or minor surfaces that are configured, for example, as curved surfaces, so as to provide beneficial results. Furthermore, it should be understood that alternative preferred embodiments may include a larger number of transducer elements in a particular embodiment of the transducer array 221. An alternative embodiment of the array 221 can provide high resolution acoustic imaging by use of a two-dimensional array of transducer elements.

As may now be appreciated, the active components of the first preferred embodiment of a probe assembly 212 are sufficiently small so as to be contained within a housing 225 that is preferably provided as a lightweight, low-profile, enclosure that is easy to manipulate by one hand. In a particularly preferred embodiment, the housing 225 includes portions thereof that are especially amenable to securing a finger grip, such as the finger grips 211 and outwardly extending ribs 226, one or both of which may be composed of resilient material that is easily grasped by the operator not only for obtaining a secure grasped of the probe assembly 212, but also for obtaining a tactile sense of the orientation of the transducer array 224 and for obtaining an adequate hold on the exterior of the housing 225 without obscuring the operator interface 213 or the sensor head 214.

With respect to the embodiment illustrated in FIGS. 2–4, the design of the probe assembly 212 will be appreciated as allowing the operator to position the sensor head 214 on a body of a medical patient by, for example, gripping the extension 219 or the ribs 226 between the thumb and forefinger of one hand. Furthermore, the operator's grasp of the extension 219 and/or ribs 226 allows the operator to achieve an immediate, ongoing sense of the orientation of the sensor head 214. Because the first embodiment of the probe assembly 212 is preferably constructed to integrate the display 218 in the probe assembly 212 at a position directly above the sensor head 214, wherein the display 218 is generally planar and is maintained in parallel with the active face of the transducer array 221, the results of any adjustments of the position and orientation of the probe assembly 212 are immediately discernible in the acoustic window effected by the display 218 in real-time. From the perspective of the operator, the image of the physical structure appears in the display 218 as if it were located directly beneath the sensor head 214.

The probe assembly 212 illustrated in FIGS. 2–4 is especially suited for use in medical diagnostic examination of the body of a patient. The size and configuration of the sensor head 214 may be dictated by the contour of the particular volume or surface onto which the sensor head 214 is to be applied. Accordingly, the overall dimensions of the housing 225, the display 218, the transducer array 221, and the sensor head 214 may vary according to configurations necessary for a variety of medical ultrasound applications. However, according to a primary teaching of the present invention, the probe assembly 212 is designed to be grasped within the fingers of one hand.

A probe assembly which is constructed for application to the throat of a human subject may be required to effect a smaller contact area than that of a probe assembly which is to be applied to the same subject's abdomen. Accordingly, as now will be understood with reference to FIGS. 5–7, and according to another teaching of the present invention, additional preferred embodiments of the transducer probe assembly may be constructed in differing sizes and configurations such that that a variety of embodiments of the transducer probe assembly are available to the operator for selection according to a particular application.

Figure 5:
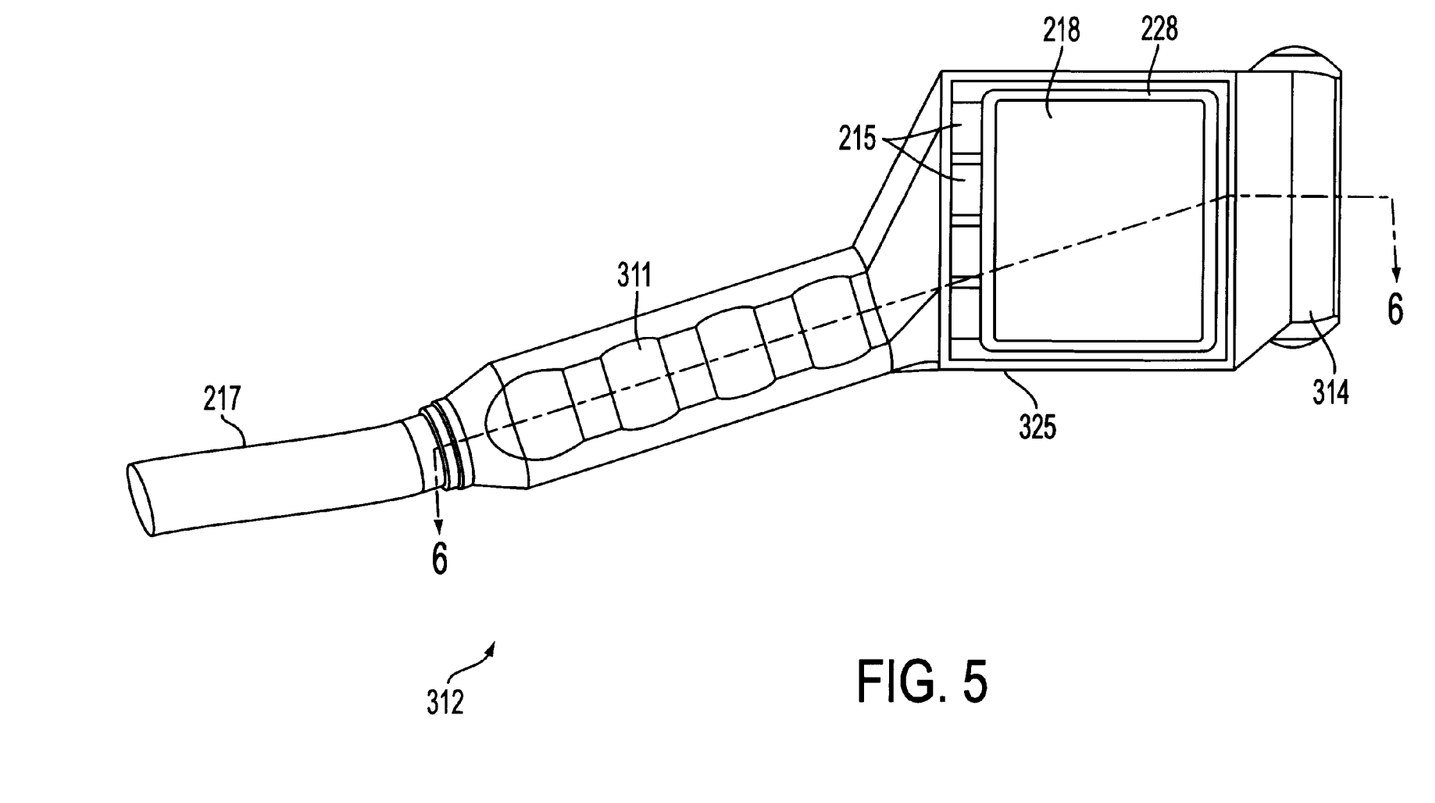
FIG. 5 is a plan view of a second preferred embodiment of a novel ultrasonic probe assembly constructed according to the present invention.
Figure 6:
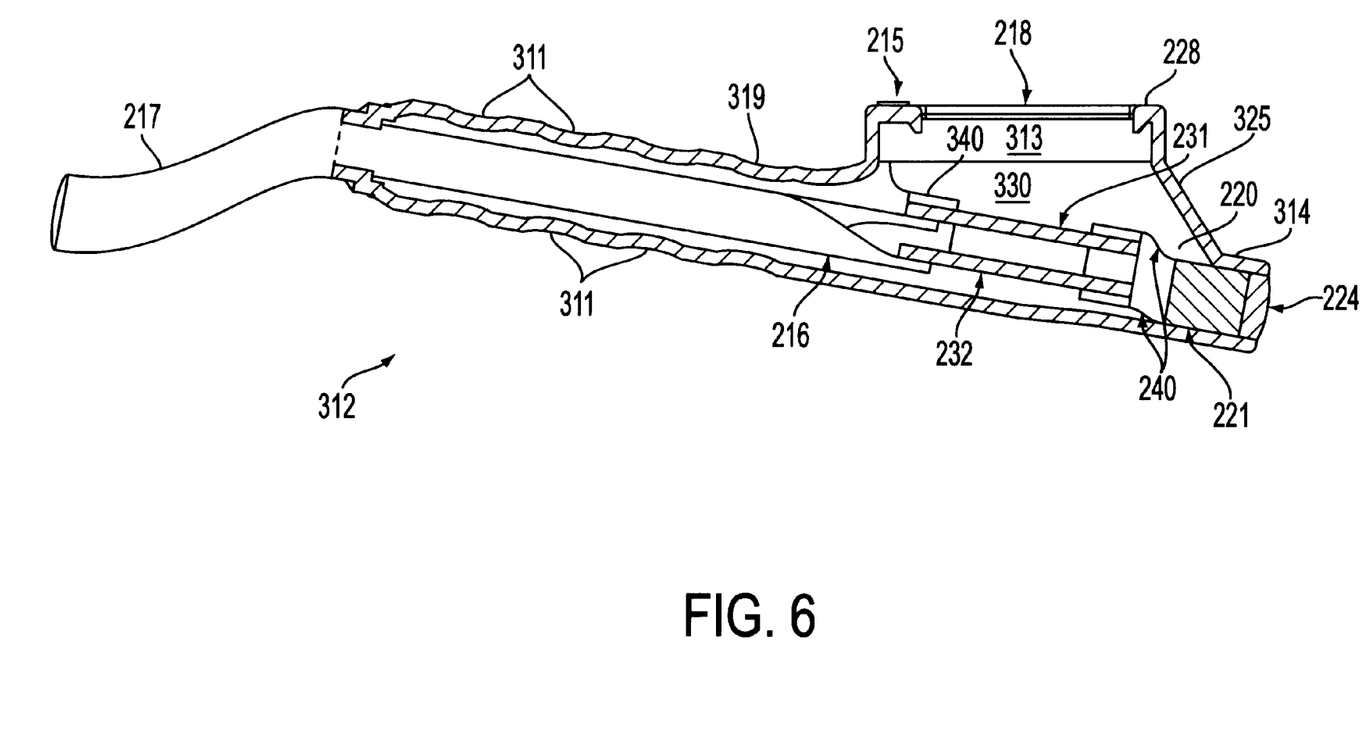
FIG. 6 is a side sectional view of the probe assembly of FIG. 5.

As shown in FIGS. 5–4, a second preferred embodiment of an ultrasonic probe assembly 212 includes a sensor head 314 containing one or more ultrasonic transducer elements for imaging physical structures in a volume of material against which the sensor head 314 is positioned. The active components of the probe assembly 312 are integrated within a stylus-shaped housing 325 and are connected to the remainder of the system 100 by way of the flexible cable 216. The active components of the probe assembly 312 include: an operator interface 313 having a display 218 and keys 215; an intermediate circuit 330 having first and second circuit boards 231, 232, and flexible circuit 340; and a transducer array section 320 that includes a transducer array 221, flexible circuits 240, and an acoustic lens 224.

The probe assembly 312 and the flexible cable 216 are joined at a tubular extension 319 of the housing 315. The extension 319 has greater length than the extension 219 described hereinabove with respect to the first preferred embodiment of the, probe assembly 212, and preferably includes a series of pairs of opposing concave portions 311, each of which are configured as a finger grip, such that the extension 319 may rest between the fingertips of one hand of the operator in a fashion similar to that employed when gripping a stylus or a pen. The flexible cable 216 includes a protective sheath 217 which preferably is sealed to the extension 319 in a fluid tight connection so as to protect the conductors within the cable 217 and the various components located within the housing 325 from the environment.

The operators grasp of the extension 319 allows the operator to achieve an immediate and intuitive understanding of the orientation of the sensor head 314. Because the probe assembly 312 is preferably constructed to integrate the display 218 in the operator interface 313 at a position rotated obliquely away from the position of the sensor head 214, wherein the major surface of the display 218 is generally planar and is laterally displaced at an approximately 90 degree angle with respect to active face of the transducer array 221, the physical structures of the region of interest that are subject to display on the display 218 may be easily viewed by the operator from an eye level that is laterally displaced from the surface against which the sensor head 314 is impressed. Although the position of the display 218 is thereby rotated away from the position of the sensor head 314, rather than in a position in parallel with the sensor head 314, the results of any adjustments of the position and orientation of the probe assembly 312 are nonetheless immediately discernible by the operator while viewing the display 218 in real-time. This lateral offset of the display 218 with respect to the sensor head 314 in the illustrated probe assembly 312 is contemplated as being useful in those circumstances wherein the operator cannot easily maintain a direct view of the display 218 if the display 218 were to be coaxial with the sensor head 314 (as illustrated in the previous embodiment shown in FIGS. 2–4). For example, the second preferred embodiment of the probe assembly 312 may be understood to have great utility in performing certain diagnostic imaging procedures with respect to the throat of a patient while the operator and the patient are positioned face-to-face. However, according to a primary feature of the present invention, the acoustic window provided in the illustrated probe assembly 312 nonetheless spatially associates, in real-time or near real-time, the displayed image of an isonified physical structure with the actual location of that physical structure.

Another embodiment of the contemplated transducer probe assembly may be required to offer more than one display in certain circumstances wherein, for example, one or more persons in addition to the operator desire a real-time view of the image. Hence, it will be appreciated that the teachings of the present invention will benefit the construction of a probe assembly having plural operator interfaces.

Figure 7:
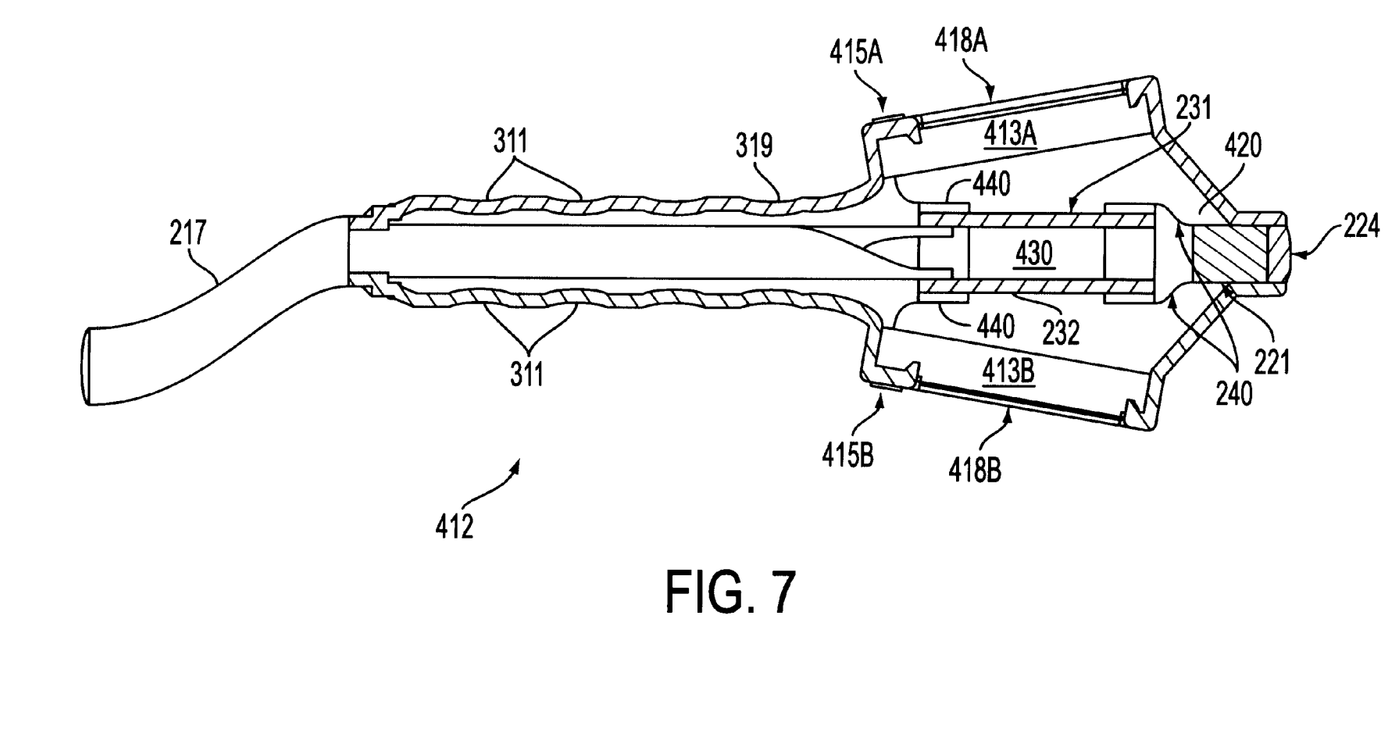
FIG. 7 is a side sectional view of a third preferred embodiment of the ultrasonic probe assembly constructed according to the present invention.

Accordingly, and with reference to FIG. 7, a third preferred embodiment of a probe assembly 412 may be constructed to include a housing 425 having a first display 418A and a second display 418B, wherein the second display 418B is preferably located in opposition with respect to the first display 418A so as to provide a respective second field of view. The active components of the probe assembly 412 include: first and second operator interface sections 413A, 413B having respective displays 418A, 418B and keys 415A, 415B; an intermediate circuit 430 having first and second circuit boards 231, 232 and flexible circuits 440; and a transducer array section 420 that includes a transducer array 221, flexible circuits 240, and an acoustic lens 224.

With respect to variations and alternative embodiments of the contemplated probe assembly, those skilled in the art will recognize that certain versions of the illustrated embodiments of a probe assembly 212, 312, 412 may be manufactured so as to withstand immersion in a sterilization chamber, and to withstand the application fluids or gels used in medical diagnostic imaging. Certain other versions of the probe assembly 212, 312, 412 may be constructed for nonmedical applications and accordingly are manufactured so as to withstand the presence of corrosive fluids, dust, debris, etc. as may be expected in an adverse environment, e.g., when deployed in an industrial setting or in the field. The illustrated embodiments of the contemplated probe assembly may also include other items known in the art, which are omitted from the Figures for clarity, such as gaskets, insulators, threaded assembly devices, transducer support structures, heat sinks, etc.

While this invention has been particularly shown and described with references to preferred embodiments thereof it will be understood by those skilled in the art that various changes in form and details may be made therein without departing from the spirit and scope of the invention as defined by the appended claims.

What is claimed is:

1. An ultrasonic imaging system for isonification of a physical structure located within a region of interest, comprising:
   a control and data processing circuit in a first housing for:
      a) performing beam forming and data-processing tasks with respect to a first signal representative of the physical structure, and
      b) generating a second signal, in response to the first signal, representative of an image of the physical structure;
   a hand-held probe assembly susceptible to being manipulated to a position adjacent to the region of interest, the probe assembly including a second housing, separate from the first housing, having integrated therein:
      a) a sensor head having therein at least one transducer element array for isonification of the physical structure and, in response, for generating the first signal, and
      b) an operator interface having therein at least one display for representing an image of the physical structure, the image being provided in response to the second signal from the control and data processing circuit, and a plurality of user activated controls to adjust at least one of the image on the display and parameters affecting the operation of the sensor head; and a cable assembly connecting the probe assembly to the control and data circuit for transfer therebetween of the first and second signals;

wherein the operator interface and the sensor head are structurally integrated within the housing so as to be co-located in a predetermined spatial relationship, said spatial relationship being aligned such that the image displayed on the operator interface may be spatially associated with the actual location of the physical structure.

2. The system of claim 1, wherein the operator interface further comprises data entry means.

3. The system of claim 1, wherein the display sits above said sensor head, relative to the physical structure during examination.

4. The system of claim 1, wherein the display is offset from the sensor head.

5. The system of claim 1, wherein the cable assembly comprises a flexible cable.

6. The system of claim 5, wherein the second housing further comprises an extension that is joined to the flexible cable.

7. The system of claim 6, wherein the second housing is an oblate shell.

8. The system of claim 6, wherein the second housing is in the form of a stylus.

9. An ultrasonic imaging system for isonification of a physical structure located within a region of interest, comprising:

a control and data processing circuit for:
 a) performing beam forming and data-processing tasks with respect to a first signal representative of the physical structure, and
 b) generating a second signal, in response to the first signal, representative of an image of the physical structure;

a hand-held probe assembly susceptible to being manipulated to a position adjacent to the region of interest, the probe assembly including a housing having integrated therein:
 a) a sensor head having therein at least one transducer element array for isonification of the physical structure and, in response, for generating the first signal, and
 b) an operator interface having therein a first and second display for representing an image of the physical structure, the image being provided in response to the second signal, wherein the first and second displays are arranged on generally opposing sides of the housing; and signal interconnection means connected to the probe assembly and to the control and data circuit for transfer therebetween of the first and second signals;

wherein the operator interface and the sensor head are structurally integrated within the housing so as to be co-located in a predetermined spatial relationship, said spatial relationship being aligned such that the image displayed on the operator interface is spatially associated with the actual location of the physical structure.

10. The system of claim 1, wherein the signal interconnection means further comprises an intermediate circuit for effecting electrical connection between the control and data-processing circuit, the sensor head, and the operator interface.

11. The system of claim 1, wherein the housing further comprises one or more finger grips amenable to being grasped by a respective one or more fingers when the housing is grasped in one hand.

12. The system of claim 1, further comprising a bezel that allows adjustment of the orientation of the display.

13. A hand-held transducer probe assembly for operation with an ultrasonic imaging system for isonification of a physical structure located within a region of interest, comprising:

a) a housing having integrated therein:
 b) a sensor head having at least one transducer element array for isonification of the physical structure and, in response, for generating a first signal, and
 c) an operator interface having therein at least one display for representing an image of the physical structure, the image being provided in response to a second signal, and a plurality of user activated controls to adjust at least one of the image on the display and parameters affecting the operation of the sensor head; and d) signal interconnection means connected to the sensor head and operator interface for transfer therebetween of the first and second signals;

wherein the operator interface and the sensor head are structurally integrated within the housing so as to be co-located in a predetermined spatial relationship, said spatial relationship being aligned such that the image displayed on the operator interface is spatially associated with the actual location of the physical structure.

14. The assembly of claim 13, wherein the operator interface further comprises data entry means.

15. The system of claim 13, wherein the display sits above said sensor head, relative to the physical structure during examination.

16. The system of claim 13, wherein the display is offset from the sensor head.

17. The assembly of claim 13, wherein the signal interconnection means further comprises a flexible cable.

18. The assembly of claim 13, further comprising a bezel that allows adjustment of the orientation of the display.

19. A hand-held transducer probe assembly for operation with an ultrasonic imaging system for isonification of a physical structure located within a region of interest, comprising:

a) a housing having integrated therein:
 b) a sensor head having at least one transducer element array for isonification of the physical structure and, in response, for generating a first signal, and
 c) an operator interface having therein a first display responsive to a second signal, for representing an image of the physical structure, and a second display, responsive to the second signal, provided in a respective second operator interface, wherein the first and second operator interfaces are arranged on generally opposing sides of the housing; and d) signal interconnection means connected to the sensor head and operator interface for transfer therebetween of the first and second signals;

wherein the operator interface and the sensor head are structurally integrated within the housing so as to be co-located in a predetermined spatial relationship said spatial relationship being aligned such that the image displayed on the operator interface is spatially associated with the actual location of the physical structure.

20. The assembly of claim 13, wherein the housing further comprises one or more finger grips amenable to being grasped by a respective one or more fingers when the housing is grasped in one hand.

21. An ultrasonic imaging system comprising:
a control and data processing circuit in a first housing that:
  a) performs beam forming and data-processing tasks with respect to a first signal representative of the physical structure, and
  b) generates a second signal, in response to the first signal, representative of an image of the physical structure;
a hand-held probe assembly including:
  a) a display unit that displays an image in response to the second signal from the control and data processing circuit;
  b) a transducer array that isonificates the physical structure and, in response to received echoes, generates the first signal, and
  c) a second housing, separate from the first housing, integrating said display unit and said transducer array so that said display unit sits above said transducer array, relative to the physical structure during examination, such that during use said display is roughly parallel with the surface of the physical structure being examined, said second housing having a gripping surface forming a periphery around said display unit and said transducer array; and
a cable assembly connecting the probe assembly to the control and data circuit for transfer therebetween of the first and second signals.

22. An ultrasonic imaging system comprising:
a control and data processing circuit in a first housing that:
  a) performs beam forming and data-processing tasks with respect to a first signal representative of the physical structure, and
  b) generates a second signal, in response to the first signal, representative of an image of the physical structure;
a hand-held probe assembly including:
  a) a display unit that displays an image in response to the second signal from the control and data processing circuit;
  b) a transducer array that isonificates the physical structure and, in response to received echoes, generates the first signal, and
  c) a second housing, separate from the first housing, integrating said display unit and said transducer array; and
a cable assembly connecting the probe assembly to the control and data circuit for transfer therebetween of the first and second signals, said cable assembly being surrounded by a protective sheath forming a single cable between said first and second housings.

23. An ultrasonic imaging system comprising:
a control and data processing circuit in a first housing that:
  a) performs beam forming and data-processing tasks with respect to a first signal representative of the physical structure, and
  b) generates a second signal, in response to the first signal, representative of an image of the physical structure;
a hand-held probe assembly including:
  a) a display unit that displays an image in response to the second signal from the control and data processing circuit;
  b) a transducer array that isonificates the physical structure and, in response to received echoes, generates the first signal, and
  c) a second housing, separate from the first housing, integrating said display unit and said transducer array such that said display unit is 70° to 110° from a scan plane of said transducer array, said second housing providing a grip extending from said display unit; and
a cable assembly connecting the probe assembly to the control and data circuit for transfer therebetween of the first and second signals.

24. An ultrasonic imaging system for isonification of a physical structure located within a region of interest, comprising:
a control and data processing circuit in a first housing for:
  a) performing beam forming and data-processing tasks with respect to a first signal representative of the physical structure,
  b) generating a second signal, in response to the first signal, representative of an image of the physical structure; and
  c) displaying an image based on the second signal; and
a hand-held probe assembly susceptible to being manipulated to a position adjacent to the region of interest, the probe assembly including a second housing, separate from the first housing, having integrated therein:
  a) a sensor head having therein at least one transducer element array for isonification of the physical structure and, in response, for generating the first signal, and
  b) an operator interface having therein a plurality of user activated controls to adjust at least one of the image on the display and parameters affecting the operation of the sensor head.

25. The system of claim 1, wherein the user activated controls are configured by the control and data processing circuit.

26. The system of claim 25, wherein the control an data processing circuit is adapted to cause the display to indicate to the user the function of the user activated controls.

* * * * *